(12) United States Patent
Desjonqueres

(10) Patent No.: US 8,507,007 B2
(45) Date of Patent: Aug. 13, 2013

(54) DERMATOLOGICAL COMPOSITION THAT CAN BE USED IN PARTICULAR FOR THE CARE AND PREVENTION OF ESCHARS

(75) Inventor: Stéphane Desjonqueres, Maisons Laffitte (FR)

(73) Assignee: Laboratoires Carilene, Montesson (FR)

( * ) Notice: Subject to any disclaimer, the term of this patent is extended or adjusted under 35 U.S.C. 154(b) by 231 days.

(21) Appl. No.: 12/736,391

(22) PCT Filed: Mar. 23, 2009

(86) PCT No.: PCT/FR2009/050496
§ 371 (c)(1),
(2), (4) Date: Oct. 25, 2010

(87) PCT Pub. No.: WO2009/125117
PCT Pub. Date: Oct. 15, 2009

(65) Prior Publication Data
US 2011/0052719 A1     Mar. 3, 2011

(30) Foreign Application Priority Data
Apr. 3, 2008 (FR) ..................... 08 52225

(51) Int. Cl.
*A61P 17/02* (2006.01)

(52) U.S. Cl.
USPC .................................... 424/555

(58) Field of Classification Search
None
See application file for complete search history.

(56) References Cited

U.S. PATENT DOCUMENTS

| | | | | |
|---|---|---|---|---|
| 4,816,254 A | * | 3/1989 | Moss | 424/642 |
| 6,001,378 A | * | 12/1999 | Desjonqueres | 424/401 |
| 2003/0175328 A1 | * | 9/2003 | Shefer et al. | 424/449 |
| 2005/0266094 A1 | | 12/2005 | Dinno | |
| 2009/0291122 A1 | | 11/2009 | Vandeputte | |

FOREIGN PATENT DOCUMENTS

| | | |
|---|---|---|
| EP | 0 117 962 | 9/1984 |
| EP | 0 225 831 | 6/1987 |
| EP | 0 225 832 | 6/1987 |
| EP | 0 225 833 | 6/1987 |
| EP | 0 226 506 | 6/1987 |
| EP | 0 293 535 | 12/1988 |
| FR | 2 461 744 | 2/1981 |
| FR | 2 539 142 | 7/1984 |
| FR | 2 797 586 | 2/2001 |
| GB | 1077378 | 7/1967 |
| WO | WO 03/041688 | 5/2003 |
| WO | 2006/087359 | 8/2006 |

OTHER PUBLICATIONS

Louise Holmen Terkelsen, et al., "Topical Application of Cod Liver Oil Ointment Accelerates Wound Healing: An Experimental Study in Wounds in the Ears of Hairless Mice", Scand J Plast. Reconstr. Hand Surg., 34, pp. 15-20, 2000.

Lotte Dann, et al., "Experimental Wounds Treated with Cod-Liver Oil and Related Substances", The Lancet, Jan. 24, 1942, pp. 95-98, XP-002509664.

C. Luley, et al., "Fettsäuren-Zusammensetzung und Peroxidationsgrad in Fischöl-und Lebertran-Präparaten, Arzneimittel-Forschung", vol. 38, No. 12, 1988, pp. 1783-1786, XP008100168, abstract only.

E. Kardash-Strochkova, et al., "Redox-potentiometric determination of peroxide value in edible oils without titration", Talanta, vol. 54, 2001, pp. 411-416, XP-002509665.

\* cited by examiner

*Primary Examiner* — Ralph Gitomer
*Assistant Examiner* — Teresa E Knight
(74) *Attorney, Agent, or Firm* — Ladas & Parry, LLP

(57) ABSTRACT

The invention relates to a composition formulated for a topical application to the skin containing, as essential constituents, peroxide lipids that have a degree of peroxidation between 30 and 500 milliequivalents per kg of peroxide lipids and cod liver oil. This composition can be used as a medical device, in order to form a protective film on the skin, especially for the care of irritated skin and/or skin that has red spots and/or skin that has superficial lesions, and/or as an adjuvant in skin massaging operations. It is most particularly useful for the care and/or prevention of eschars.

26 Claims, No Drawings

DERMATOLOGICAL COMPOSITION THAT CAN BE USED IN PARTICULAR FOR THE CARE AND PREVENTION OF ESCHARS

This application is a 371 of PCT/FR2009/050496 filed on Mar. 23, 2009.

The present invention relates to a novel composition formulated for topical application to the skin, and relates to its use in particular for the care and prevention of bed sores.

Various peroxidized lipids are known, in particular obtained by peroxidation of natural vegetable oils. Such peroxidized lipids and their uses are described in the following patents: BSM N° 2 330 M, EP-A-0 293 535, FR-A-2 591 112, EP-A-0 225 831, EP-A-0 225 832, EP-A-0 225 833, EP-A-0 226 506, FR-A-2 461 744, FR-A-2 539 142, and EP-A-0 117 962, that relate either to the preparation of such peroxidized lipids, or to their applications in various fields, in particular in the care of certain disorders in the field of rheumatology or traumatology, or even as substances that participate in the healing process.

Above-mentioned European patent EP 0 293 535 in particular, describes using peroxidized lipids to repair the vulnerable skin of people who are in a prone position for long periods of time, which leads in the end to bed sores, and that constitutes real concern, both for the patient who suffers and for the hospital staff who seek to relieve such suffering. A bed sore is necrosis of the skin, created by a lack of vascularization, both of the capillaries and of the veins and the arteries, as a result of the patient's skin surface being compressed against the surface on which the patient is lying.

As disclosed in patent EP 0 293 535, using peroxidized oils for repairing the vulnerable skin of people who are in a prone position constitutes a particularly effective means of caring for and preventing bed sores, in particular by massaging the zone to be treated with that substance.

Currently, there exists intense research for developing substances that make it possible to improve a pathological condition by the intervention of a mechanical action on its own and without pharmacological action.

Examples of such substances that may be mentioned include substances that are formulated so as to act like a dressing to create an isolating barrier on the surface of a wound, so as to enable natural healing of the wound by isolating it from the external environment.

Another example of fields in which it is desired to have substances that act on a painful condition solely by a mechanical effect, is the field of therapeutic massage. It is well known that a certain number of painful or pathological conditions respond favorably to massaging action. However, the massage is much more effective when it is performed in a mechanical environment that is favorable, in particular that encourages the masseur's hands to slide over the surface of the body being massaged. Often, it is also desirable to make the massage more gentle, and to avoid any irritation of the skin during repeated or lengthy massaging. To this end, it is common place to use additives such as talcs that are processed to a greater or lesser extent, for making massaging easier.

In the context of his research into novel means of improving pathological conditions by the intervention of a mechanical action on its own, the inventor of the present invention has discovered, and described in application FR 279 97586, that peroxidized lipids can be used in particularly effective manner as agents for forming a lipidic film on the surface of the skin, and that the formation of the lipidic film makes it possible, in remarkable manner, to improve a certain number of pathological conditions, in particular by a protective effect that provides an improvement in the healing of wounds, and the treatment of various erythemas. More generally, it turns out that the lipidic film formed by peroxidized lipids is particularly effective in any application in which it is desired to isolate the skin from the external environment so as to improve its qualities, in particular its biomechanical qualities.

It also turns out that peroxidized lipids can be used as massage additives in connection with forming a particularly effective film on the part of the body that is to be massaged either before or during massaging, thereby making "sliding" easier during massaging.

That type of action turns out to be particularly advantageous at a period in which it is desired to find treatment methods that are aggressive towards the organism as little as possible. Such treatments further make it possible to satisfy European Community Regulations regarding medical devices, since a particular chapter specifies that said devices cover substances that make it possible to expect health benefits that are associated with substances for local usage, solely by the mechanical effect associated with their use.

Administering cod liver oil by mouth has been well known for a long time since that oil has been used for a long time to ensure good development in children, in particular with regard to the skeleton, the nervous system, and intellectual development. Administration by mouth is still practiced, however with formulations, e.g. in the form of capsules, that avoid the disadvantages associated with the particularly strong odor of cod liver oil.

In addition to being used internally, cod liver oil has also been described for its advantages in topical application. It has thus been stated in literature that cod liver oil can encourage the healing of wounds and the quality of the skin.

Thus, "Topical application of cod liver oil ointment accelerates wound healing: an experimental study in wounds in the ears of hairless mice", Scand J. Plast Reconstr Hand Surg 34: 15-20, 2000, describes the effect of topical application of cod liver oil on the speed of epithelialization and of neovascularization on a hairless mouse model, and the effect of local application of vitamin A on the same model.

That study confirms the healing effect of cod liver oil and seeks to explain this activity, that seems to be associated with the presence of high quantities of vitamin A in the cod liver oil.

It is well known that vitamin A is used in numerous cosmetic applications for its activity in making keratinization of the skin more regular, and in bringing modifications to the dermis, by acting on the metabolism of fibroblasts.

However, without doubt, this envisaged use of cod liver oil has been severely held back as a result of the disagreeable odor of the substance, in spite of the oil being subjected to treatments for diminishing its disagreeable odor.

Continuing with his studies, with a view to improving the prevention and care of bed sores, and also to improving the result and the conditions of massaging the skin, as well as the care of skin that is irritated and/or that presents redness and/or that presents surface lesions, while avoiding the use of compositions that cause a pharmacological, metabolic, or immunological effects, the inventor has now discovered that it is possible to improve still further the effectiveness of peroxidized oils as already described, by combining them with cod liver oil, in particular in proportions that make it possible to benefit from the advantages of both types of substance, further avoiding the well known drawback of cod liver oil, which is its odor, in particular as a result of the cod liver oil being genuinely diluted in the peroxidized oil.

The inventor of the present invention has observed that it is possible to improve greatly the results obtained by topical application of peroxidized vegetable oil-based compositions, in particular in massaging operations, and very particularly in the treatment of bed sores, by mixing the oils with cod liver oil. The composition obtained in this way presents the advantages of both types of oil, while minimizing the drawbacks associated with using cod liver oil, and very particularly its odor.

It has thus been found that the two types of oil can act in synergy, being completely miscible one in the other, as a result of the very close rheological properties of the two types of oil.

It has thus been made possible to prepare oily compositions that are viscous to a greater or lesser extent, in particular gels or mixed gels or emulsions that present both the advantages of the peroxidized oil-based compositions described in the above-mentioned literature, and the advantages of cod liver oil, which in addition to its healing properties on the skin, has the advantage of bringing essential fatty acids to the skin that are not found in sufficient quantity in peroxidized vegetable oils, in particular omega-3 acids, or alpha-linolenic acid and omega-6, or linolenic acid. These two types of fatty acid, known as essential fatty acids, enable the organism to synthesize other essential fatty acids.

A very particular advantage of compositions of the invention is that they do not cause any pharmacological, metabolic, or immunological effect, since they do not contain pharmacological compounds, and are constituted essentially by peroxidized lipids (oxidized glycerol triesters) and by cod liver oil, the other ingredients possibly being essentially water, aromas or fragrances, preservatives, or agents for controlling the viscosity of the composition so as to improve topical application to the skin.

A particular advantage of this type of composition and of the action method implemented during its application (formation of a lipidic film on the zone to be treated) is that they turn out to be particularly advantageous at a time in which it is desired, very particularly, to find treatment methods that are as little aggressive as possible for the organism. These compositions further make it possible to satisfy the European Community Regulation regarding medical devices, and the US Food and Drug Administration Regulation regarding monograph products or medical devices.

Thus, in a first aspect, and as a novel industrial product, the invention provides a composition formulated for topical application to the skin, said composition being characterized in that it contains, as essential ingredients, cod liver oil and a peroxidized oil of vegetable origin or a mixture of peroxidized oils of vegetable origin presenting a level of peroxidation comprised between 30 milli-equivalents per kilogram (mEq/kg) and 500 mEq/kg.

In a second aspect, the invention provides a medical device that is constituted by a composition of the first aspect.

In a third aspect, the invention provides the use of a combination of cod liver oil and peroxidized oil(s) for preparing a medical device of the second aspect, said medical device acting so as to form a protective film on the skin, in particular for the care of skin that is irritated and/or that presents redness and/or that presents surface lesions, and/or being used as an additive in skin-massaging operations.

The invention also provides a medical device that acts so as to form a protective film on the skin, in particular for the care of skin that is irritated and/or that presents redness and/or that presents surface lesions, and/or that is used as an additive in skin-massaging operations, in particular for the care and/or prevention of bed sores.

Finally, the invention also provides a method of treating the human body, said method comprising applying a composition of the first aspect, or a medical device of the second aspect.

The method serves to form a protective film on the skin, in particular for the care of skin that is irritated and/or that presents redness and/or that presents surface lesions, and/or for use as an additive in skin-massaging operations, in particular for the care and/or prevention of bed sores.

In the meaning of the invention, the term "essential ingredients" should be understood to mean that the cod liver oil and the peroxidized vegetable oil or the mixture of peroxidized vegetable oils are the basic ingredients of the composition.

As a result of their compatibility, these two ingredients make it possible to form, on the skin to be treated, a lipidic film that acts as a genuine dressing. Within the protection of the dressing, natural regeneration of the skin is accelerated, and healing is thus made easier.

In addition, in particular when in the form of an oil or in the form of an oily gel, and as a result of the presence of the two types of compatible substances that are oily, the composition has an essential advantage of encouraging "sliding" during a massaging operation.

The composition of the invention may also contain water, in particular in a quantity that is sufficient for the solution to be in the form of an oil-in-water type emulsion, or that is sufficient to form with the cod liver oil and the peroxidized oil or the mixture of peroxidized oils, a "mixed-gel" type gel, in the presence of a viscosification agent.

In the meaning of the invention, the term "mixed gel" should be understood to mean an oil and water based gel, the oil here being constituted by the cod liver oil and the peroxidized oils contained in the composition of the invention.

In addition to the essential ingredients that are the active ingredients, cod liver oil and peroxidized oil(s), and possibly water, the composition of the invention may contain various additives, in particular such as fragrances or aromas selected as a function of the application of the composition, preservatives, and agents for controlling the viscosity of the composition.

The composition may further contain various formulation additives, in particular for improving its galenic form, for making application easier, or for improving protection of the composition.

In conventional manner, such formulation additives are emulsifying agents, emulsifiers, surfactants, wetting agents, emollients, preservatives, and antioxidants.

The peroxidization level of the peroxidized vegetable oil or of the mixture of peroxidized vegetable oils is measured in accordance with the ISO 3960 standard.

In order to prepare the compositions of the present invention, peroxidized vegetable oils or mixtures of oils are selected presenting a level of peroxidation comprised between 30 mEq/kg and 500 mEq/kg. In more advantageous manner, the level of peroxidation comprised between 50 mEq/kg and 300 mEq/kg, more preferably between 50 mEq/kg and 150 mEq/kg.

Examples of vegetable oils that may be selected for the invention and that may be mentioned are sweet almond oil, hazelnut oil, peanut oil, corn oil, grape seed oil, sesame oil, and safflower oil. It is also possible to use a mixture of these oils.

In a particularly preferred variant of the invention, peroxidized corn oil is selected presenting a level of peroxidation comprised between 30 mEq/kg and 500 mEq/kg.

In the invention, the main ingredients, generally representing at least 80% by weight of the oils or mixtures of vegetable oils used are advantageously constituted by triglycerides that satisfy the formula:

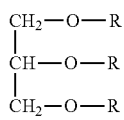

in which the radicals R are mainly represented by partially peroxidized $C_{18}$ unsaturated acids (as a function of the level of peroxidation of said oil).

The composition of the invention advantageously contains from 0.5% to 20%, preferably from 1% to 10%, by weight of cod liver oil.

In an advantageous variant of the present invention, the cod liver oil used has previously been subjected to a treatment for reducing odors, and very particularly a cold refining treatment, preferably a winterizing treatment. Such cod liver oils are commercially available.

Advantageously, the compositions of the invention are in the form of an emulsion or of a gel.

When the composition is in the form of an emulsion, it is advantageously an oil-in-water type emulsion. In such an emulsion, the oily phase is constituted by cod liver oil and by peroxidized oil or peroxidized oils, and advantageously represents from 1% to 25% by weight of said composition.

When the composition is in the form of a gel, it may be an oily gel or a mixed gel.

The cod liver oil and the peroxidized vegetable oil or the mixture of peroxidized vegetable oils constitute the oil of the oily gel. The gel further contains an agent that makes it possible to obtain the viscosity desired for good topical application of the gel. The viscosity agent is preferably colloidal silica. The gel may possibly contain one or more preservatives and/or a fragrance or an aroma, selected as a function of the type of application desired. In general, the gel may also contain any additive of formulation that is conventionally used in the field.

Naturally, the fragrance or the aroma is selected as a function of the type of application envisaged.

The composition may also be in the form of a mixed gel.

Advantageously, such a gel is obtained from: cod liver oil; a peroxidized vegetable oil or a mixture of peroxidized vegetable oils; water; and a gelling agent, preferably a hydrophilic-type gelling agent. The mixed gel advantageously contains from 1% to 25% by weight of oily-type substances (cod liver oil and peroxidized oils).

The mixed gel could possibly further contain at least one agent selected from preservatives, fragrances or aromas, and emulsifying agents.

As described above, the composition of the invention presents the advantage of constituting a medical device.

More precisely, the composition of the invention, when it is applied to the skin, makes it possible to form a protective film on the skin suitable for caring for the skin when it is irritated and presents redness or surface lesions. The film also presents the advantage of aiding massaging action on the skin, by encouraging the fingers to slide over the skin.

Thus, the composition of the invention may advantageously be used as a medical device in any action in which it is desired to deposit a protective film on the skin and/or to encourage massaging action in order to facilitate skin regeneration.

In particular, the composition may be used for the care of skin that is irritated and/or that presents redness and/or that presents surface lesions, to care for any injured or inflamed skin: small wounds, grazes, irritations, abrasions, burns . . . .

An example of an application in which the composition of the invention turns out to be particularly advantageous is that of the prevention and/or care of bed sores. The composition is very rich in lipidic compounds, and has a very great constitutional affinity with the skin. It protects it, and restores the injured portions. In addition, it forms a lipidic film that acts as a dressing, within the protection of which cell multiplication is accelerated. Essential fatty acids contained within the composition are elements that are essential for the biosynthesis mechanisms of tissue regeneration.

In all of the applications envisaged, a reduction in inflammation, rapid soothing with disappearance of the burning or itching sensation, and an acceleration of the healing process have been observed during tests performed on volunteers.

EXAMPLE

In the following example, the proportions given are expressed as percentages by weight.

The composition contains:

|  | % |
|---|---|
| Peroxidized corn oil presenting a level of peroxidation comprised between 50 mEq/kg and 300 mEq/kg | 91.1% |
| Winterized cod liver oil | 5.00% |
| Phenoxyethanol-parabens | 0.9% |
| Fragrance | 3.0% |

This composition was packaged in glass bottles that were provided with atmospheric metering pumps (without propellant gas) to deliver substance in a dose that was appropriate and always identical.

This composition was used in the prevention of bed sores.

A clear improvement was observed in the reddened pressure area of patients who were prone and who were at risk of bed sores appearing.

A light massage with this composition, performed twice a day by effleuring the concerned area of skin (with the ends of the fingers), made it possible to prevent bed sores from forming, and made it easier to provide care and massage.

These tests were performed on about twenty volunteers who were hospitalized for a long stay.

The invention claimed is:

1. A composition formulated for topical application to the skin, comprising:
   Cod liver oil and a peroxidized oil of vegetable origin, or
   Cod liver oil and a mixture of peroxidized oils of vegetable origin, said peroxidized oil or mixture of peroxidized oils of vegetable origin presenting a level of peroxidation comprised between 30 mEq/kg and 500 mEq/kg.

2. The composition according to claim 1, wherein said peroxidized oil or said mixture of peroxidized oils presents a level of peroxidation comprised between 50 mEq/kg and 300 mEq/kg of said peroxidized oil or of said mixture of peroxidized oils.

3. The composition according to claim 1, wherein the main ingredients of said peroxidized oil or said mixture of peroxidized oils include partially oxidized triglycerides of the general formula:

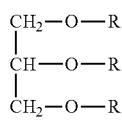

in which the radicals R are partially peroxidized $C_{18}$ unsaturated acids.

4. The composition according to claim 1, wherein the natural oil is selected from the group consisting of sweet almond oil, hazelnut oil, peanut oil, corn oil, grape seed oil, sesame oil, and safflower oil, and mixtures thereof.

5. A composition formulated for topical application to the skin, comprising:
   Cod liver oil and a peroxidized oil of vegetable origin, or
   Cod liver oil and a mixture of peroxidized oils of vegetable origin,
   said peroxidized oil or mixture of peroxidized oils of vegetable origin presenting a level of peroxidation comprised between 30 mEq/kg and 500 mEq/kg, and comprising from 0.5% to 20% by weight of cod liver oil.

6. The composition according to claim 1, which is in the form of an oil-in-water type emulsion, the oily phase of said emulsion comprising cod liver oil and said peroxidized oil or said mixture of peroxidized oils, and representing from 1% to 25% by weight of said composition.

7. The composition according to claim 1, which is in the form of an oily gel.

8. The composition according to claim 7, wherein said oily gel comprises:
   a first ingredient selected from the group consisting of:
      cod liver oil and peroxidized oil, and
      cod liver oil and said mixture of peroxidized oils, and
   a gelling agent.

9. The composition according to claim 8, further comprising at least one agent selected from the group consisting of preservatives, fragrance or aroma, and additives.

10. The composition according to claim 1, which is in the form of a mixed gel which comprises:
    a first ingredient selected from the group consisting of:
       cod liver oil and peroxidized oil, and
       cod liver oil and said mixture of peroxidized oils,
    water, and
    a hydrophilic-type gelling agent,
    said mixed gel containing from 1% to 25% by weight of said first ingredient.

11. The composition according to claim 10, which further comprising at least one agent selected from the group consisting of preservatives, fragrances or aromas, and emulsifying agents.

12. A medical device comprising a composition according to claim 1.

13. A method for forming a protective film on the skin, comprising the application to the skin in need thereof, of a composition according to claim 1.

14. The method according to claim 13, wherein the skin is selected from irritated skin, skin that presents redness, and skin that presents surface lesions.

15. The method according to claim 13, for the care or prevention of bed sores, or both.

16. A method for using as an additive in massaging operations, comprising the application to the skin in need thereof, of a composition according to claim 1.

17. The method according to claim 16, wherein the skin is selected from irritated skin, skin that presents redness, and skin that presents surface lesions.

18. The method according to claim 16, for the care or prevention of bed sores, or both.

19. A method for forming a protective film on the skin, comprising the application to the skin in need thereof, of a medical device according to claim 12.

20. The method according to claim 19, wherein the skin is selected from irritated skin, skin that presents redness, and skin that presents surface lesions.

21. The method according to claim 19, for the care or prevention of bed sores, or both.

22. A method for using as an additive in massaging operations, comprising the application to the skin in need thereof, of a medical device according to claim 12.

23. The method according to claim 22, wherein the skin is selected from irritated skin, skin that presents redness, and skin that presents surface lesions.

24. The method according to claim 22, for the care or prevention of bed sores, or both.

25. A composition formulated for topical application to the skin, comprising:
    Cod liver oil and a peroxidized oil of vegetable origin, or
    Cod liver oil and a mixture of peroxidized oils of vegetable origin,
    said peroxidized oil or mixture of peroxidized oils of vegetable origin presenting a level of peroxidation comprised between 30 mEq/kg and 500 mEq/kg, and
    comprising from 1% to 10% by weight of said cod liver oil.

26. A composition formulated for topical application to the skin, comprising:
    about 91% by weight peroxidized corn oil; and
    about 5% by weight cod liver oil.

\* \* \* \* \*